(12) United States Patent
Fuchs

(10) Patent No.: US 6,179,164 B1
(45) Date of Patent: Jan. 30, 2001

(54) DISPENSER FOR MEDIA, PARTICULARLY POWDER

(75) Inventor: Karl-Heinz Fuchs, Radolfzell (DE)

(73) Assignee: Ing. Erich Pfeiffer Gmbh, Radolfzell (DE)

( * ) Notice: Under 35 U.S.C. 154(b), the term of this patent shall be extended for 0 days.

(21) Appl. No.: 09/291,723

(22) Filed: Apr. 14, 1999

(30) Foreign Application Priority Data

Apr. 18, 1998 (DE) .............................. 198 17 417

(51) Int. Cl.⁷ .................................................. B67D 5/00
(52) U.S. Cl. .......................................... 222/82; 222/321.9
(58) Field of Search ........................ 222/82, 83, 321.7, 222/321.9, 321.2

(56) References Cited

U.S. PATENT DOCUMENTS

| 4,565,302 | 1/1986 | Pfeiffer et al. ........................ 222/38 |
| 5,469,989 | 11/1995 | Graf et al. ............................. 222/82 |
| 5,964,417 | * 10/1999 | Amann et al. ....................... 239/338 |

FOREIGN PATENT DOCUMENTS

| 3625685 C2 | 3/1987 | (DE) . |
| 3927170 A1 | 8/1989 | (DE) . |
| 4118674 A1 | 6/1991 | (DE) . |
| 4128295 A1 | 8/1991 | (DE) . |
| 4340768 A1 | 11/1993 | (DE) . |
| 4400084 A1 | 1/1994 | (DE) . |
| 195 02 725 A1 | 8/1996 | (DE) . |
| 197 04 849 A1 | 8/1998 | (DE) . |
| 0796628 A2 | 9/1997 | (EP) . |

* cited by examiner

Primary Examiner—Philippe Derakshani
(74) Attorney, Agent, or Firm—Quarles & Brady LLP

(57) ABSTRACT

A dispenser (1) comprises two actuating units (2, 3) and within these actuating units (2, 3) an intermediate unit (4) which is axially shiftable relative to the actuating units (2, 3). The intermediate unit (4) receives the premeasured does of powder in a blister (5) and includes setting means (30) for forwarding the blister (5). The intermediate unit (4) further has a cylinder (51) of a pump (51), control means (79) for an outlet valve (9) of said pump (51) and means (75) for preventing withdrawal from the first unit (2). On discharge the medium is under precompression and directed into powder chamber (14) which previously was torn open by opening means (20). For replacing the blister (5) a lid (6) is tilted sidewards.

29 Claims, 3 Drawing Sheets

DISPENSER FOR MEDIA, PARTICULARLY POWDER

TECHNICAL FIELD AND BACKGROUND OF THE INVENTION

The invention relates to a dispenser for media which may be at least partly solid or flowable, in forms such as liquid, pasty and/or gaseous. Preferably, the media are grainy or powdery and thus suitable as bulk media. The dispenser is held single-handedly and is simultaneously operated with the fingers of one hand. Thus, the pharmaceutical, cosmetic or similar media are expelled. Such media may be designed for application to the respiratory tract, that is, for nasal or oral administration.

The dispenser may be provided for a single discharge action or a single unidirectional operating stroke. Thus, return means for returning the dispenser from the end position to the initial or rest position may be omitted. The dispenser may also permit several actuating strokes in sequence, each restarting from a different position or the above-mentioned rest position.

For discharging minutely dosed medium quantities of as high as 30, 20, 15 or 12 mg and as low as 5 mg, highly compact dispensers suffice. Although the reservoir chamber containing the medium premeasured for a single discharge dose may be an elongated capsule or cup, it is, however, of advantage to shape it as a flat tray and/or spherically domed. Thus, the medium is flushed out of the open reservoir chamber by a second or conveying medium such as a liquid, gas or air. The dosing medium is thereby atomized in the second medium to achieve a uniform distribution and singling of the particles up to the exit from the medium outlet.

The cup depth of the reservoir chamber may be less than 7, 5 or 4 mm and more than 2 mm. Its largest diameter is less than 20, 15 and 10 mm and more than 3 or 6 mm or greater than the cup depth. The reservoir is replaceable after having been emptied of its contents. The chamber volume of the reservoir is filled only partly with medium to facilitate its loosening right from the start of discharge. The reservoir or magazine body may be dimensionally stable or flexibly bendable in the zones connecting to the rigid chamber. It is made in the form of a transparent or non-transparent or non-translucent blister having film-thin walls. Prior to discharge, the filled reservoir chamber is sealed to be pressure-tight and sterile. The closure is formed by an adhesively or hot-sealingly attached film of plastic, or a metal foil such as aluminum. The foil, which is planar, covers the chamber opening and sealingly adjoins the chamber body directly up to the bounds of the chamber opening as well as full-length about the circumference thereof. Thus, no medium can enter between chamber body and closure from the chamber. Reference is made to the German Patent Application 197 04 849, published Aug. 13, 1998, U.S. Pat. No. 5,964,417, issued Oct. 12, 1999 and the German Laid-Open Document 195 02 725, laid open Aug. 1, 1996, including the features and effects described therein in the present invention.

OBJECTS OF THE INVENTION

An object of the invention is to provide a medium dispenser which avoids the disadvantages of prior art configurations or assures the advantages of the cited configuration. Another object is to permit translation of the reservoir into various function postures, for example, for sequentially triggering various functions of the dispenser. A further object is to endow the dispenser with a high conveying power for a small stroke. Still another object is to facilitate replacement of the reservoir or a magazine. Other and further objects of the invention will be obvious upon an understanding of the illustrative embodiment about to be described, or will be indicated in the appended claims, and various advantages not referred to herein will occur to one skilled in the art upon employment of the invention in practice.

SUMMARY OF THE INVENTION

The invention provides for operationally producing a functional motion of the reservoir in the course of a discharge cycle or an associated actuation. Such a motion may be a linear stroke motion, an indexing motion oriented transverse thereto or an opening motion oriented transverse to the indexing. Due to the indexing motion, the reservoir is moved from a protected starting position of the reservoir chamber into the position determined for discharge. Due to the opening motion a wall, particularly a chamber lid providing an outlet closure, is provided with an outlet opening for the medium. Due to the stroke motion the complete dispenser may be shortened so that it is particularly well held in the hand during discharge. The opening motion commences just before or together with the indexing motion which ends either before the opening member engages the closure of the reservoir chamber or thereafter, but before the opening motion ends. In the latter case the opening member, while already engaging the closure, executes two motions oriented transverse to each other. Thus, the closure is opened particularly effectively or over a large width. The stroke motion may be used to control or open a further outlet closure, or valve, to convey the second medium, to limit the operating motion or stroke, to prime the second medium or the like.

A reservoir support exchangeably accommodating the reservoir is synchronously movable with the reservoir, particularly over the functional stroke, not over the working stroke but, where necessary, over the indexing motion. The reservoir support may form a boundary or cylinder or plunger of a compression chamber or pump chamber, may comprise the opening member for the outlet closure, may form the stop, may constrict an outlet duct for the second medium leading to the reservoir chamber and being constricted prior to flow commencement of this medium, may form a counter for counting the discharge cycles or may form an indicator of the counter, may improve or stiffen the mutual mounting of the two bases or casing units, may bound an annular chamber adjoining an outermost dispenser wall, may form an abutment for a return spring or a downholder for the reservoir, may movably or rotatably but centrally receive the reservoir, may cause a resilient tensioning relative to one of the base units and transverse to the stroke, etc.

In operation the reservoir or reservoir support is entirely enclosed within a housing. The casing parts thereof are formed directly by the two base units. For exchanging the reservoir or to render it manually accessible the housing needs to be opened. Instead of entirely separating the two housing parts, one of the housing parts comprises an access opening which is closed off in operation by a lid, such as an end lid. This lid includes a stud having the medium outlet, the opening member, a setting member of the positioner, means for positioning the reservoir without motion play, an actuating handle, an abutment for a spring or the like. The lid may be located axially mountable, radially insertable or pivotable on the associated housing part and bound that part of the outlet duct for the second medium which leads to the reservoir chamber or that outlet duct which leads from the reservoir chamber to the medium outlet. All of these functions may be caused by a one-part or multi-part component. The associated remaining housing part centers the reservoir or reservoir support which prevents withdrawal and which disables the axial withdrawal of the associated unit from the other unit. Additionally this housing part may directly drive the reservoir or reservoir support over the associated stroke path relative to the other housing part. In the closed position the lid and the associated housing part are mutually positionally secured via a snap connector causing a seal.

The indexing motion may be caused by mutually axially mating circumferential serrations having slanting flanks like the counter means. Reference is made to U.S. Pat. No. 4,565,302, issued Jan. 21, 1986, for including further features and effects described therein in the present invention.

BRIEF DESCRIPTION OF THE DRAWINGS

Example embodiments of the invention are explained in more detail in the following and illustrated in the drawings in which.

DETAILED DESCRIPTION

Figure 1:
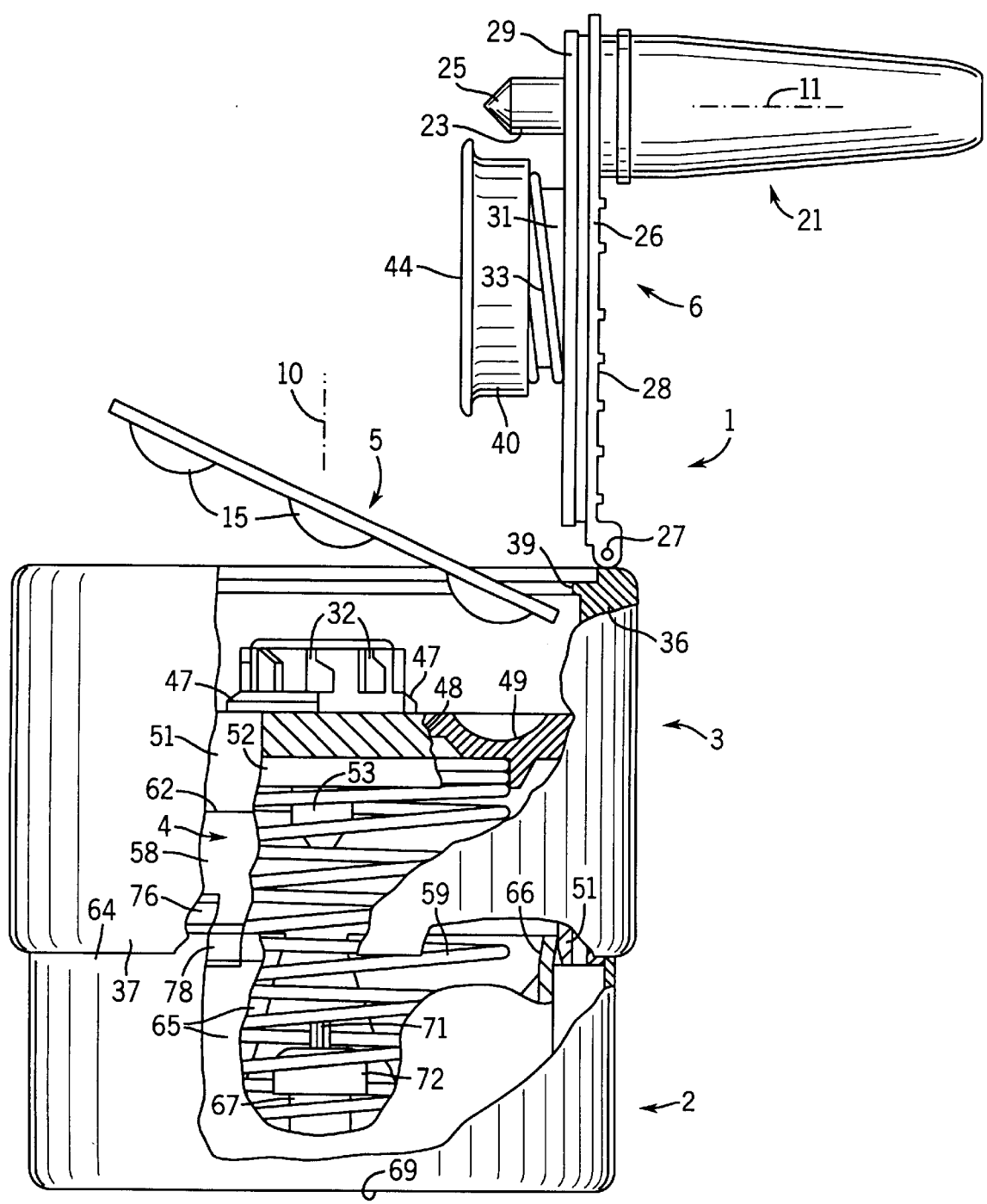
FIG. 1 is a partial axial section through a dispenser according to the invention when in the starting position and in the opened position for changing the magazine.

FIG. 1 shows a dispenser 1 comprising two basic units 2, 3 manually axially movable relative to each other, forming the mutually remote ends of the dispenser and compressible for shortening the dispenser 1. Units 2, 3 form a housing internally entirely receiving a further unit 4. The outer diameter of unit 4 equals the largest inner diameter of first unit 2. The length of unit 4 corresponds to at least a third or half of the spacing between the large outer end faces or handles of units 2, 3. A further unit 5 or a reservoir is located entirely within the base 2, 3 or housing and between opposing end faces of units 3, 4. Unit 5 extends axially significantly less than each of units 2 to 4. Units 4, 5 are movable relative to and independent of each other but also commonly relative to each of units 2, 3, namely both axially and in a transverse or rotational motion. Units 2, 3 are permanently prevented from mutual rotation. A further unit 6 is movable relative to each of units 2 to 5 and commonly with unit 3. Unit 6 forms a sub-unit of unit 3, namely a removable or hinged lid of the housing.

Figure 2:
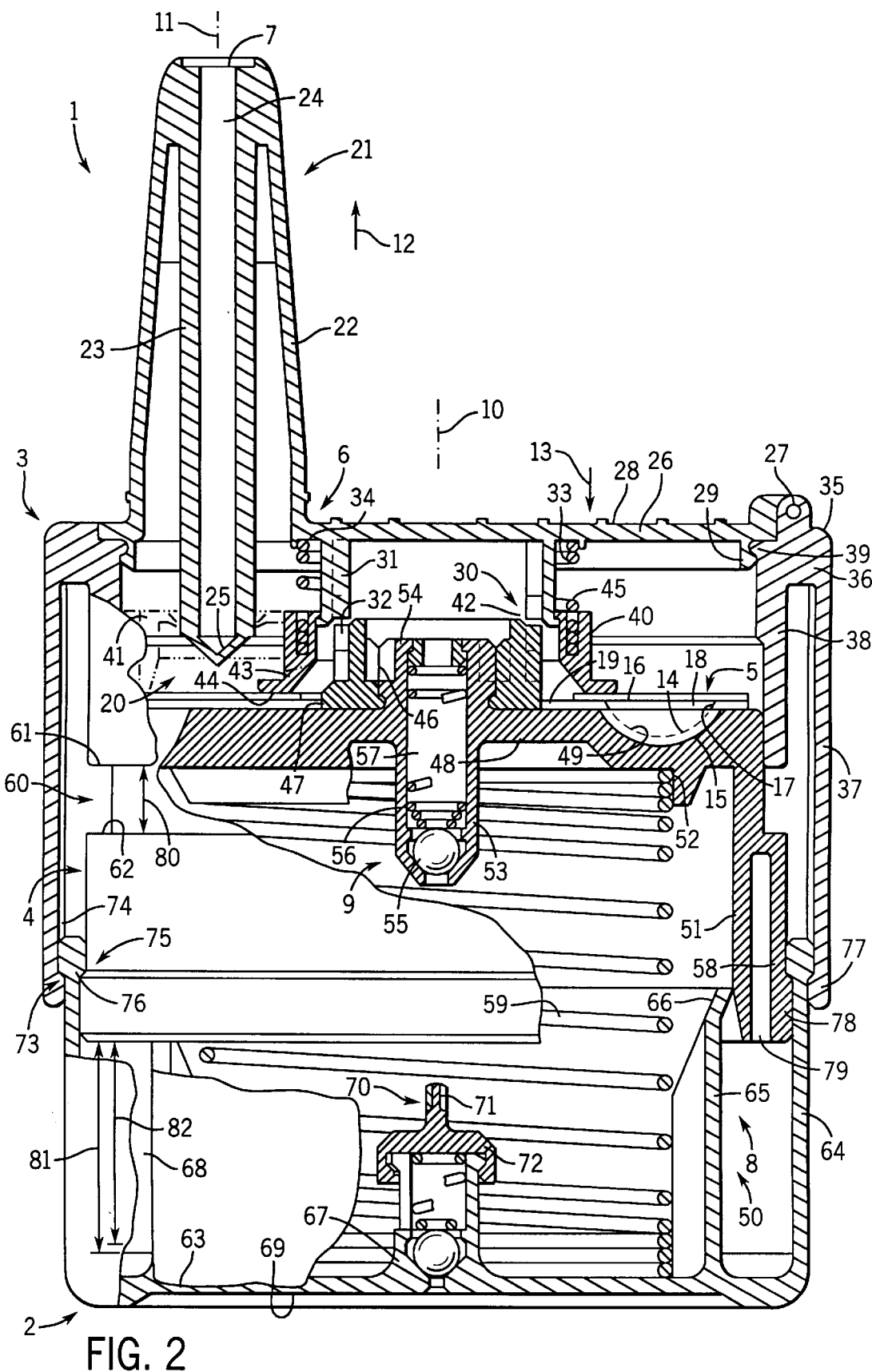
FIG. 2 is an enlarged view of the dispenser shown in FIG. 1, but in the closed condition.
Figure 3:
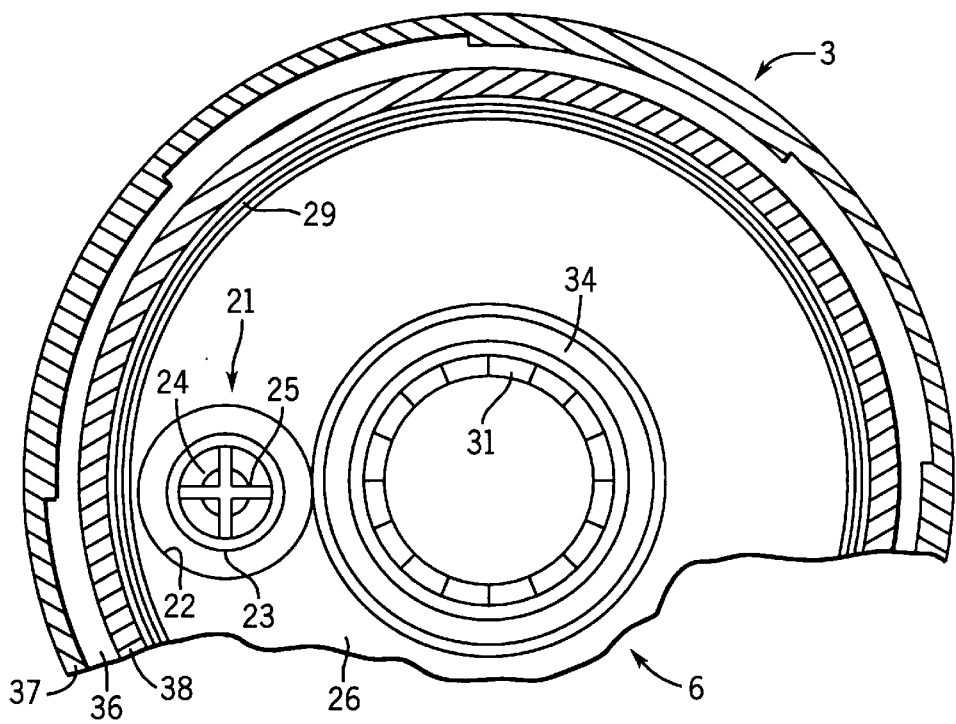
FIG. 3 is a transverse cross-sectional view looking upwards through the dispenser.

Medium outlet 7 porting to the environment is movable commonly with each of units 3, 6 and relative to units 2, 4, 5. Reservoir assembly 8 is provided totally within housing 2, 3. Reservoir assembly 8 delivers a conveying or second medium, such as air. The second medium is supplied firstly to the medium and then to outlet 7 via an outlet closure 9 or resiliently closed valve. Axis 11 of the outlet 7 is eccentric, but axially parallel to the center or main axis 10 of units 2 to 5 and closely adjacent to their outermost circumferences. The first medium flows within units 2, 4 and 5 and upstream of outlet 7 parallel to axes 10, 11 in direction 12 away from unit 2. Thus it leaves the dispenser 1 in direction 12. From the starting position shown in FIG. 2 and for actuation units 3 to 6 are manually moved in axial direction 13 relative to unit 2.

Reservoir 5 has a deep-drawn or injection-molded one-part base body including a plurality of chamber bodies 15, in this case eight in number. Bodies 15 are uniformly distributed about axis 10. Reservoir 5 also has a separate planar outlet closure or foil closure 16. Each chamber body 15 forms a spherical cap or reservoir chamber 14. Chamber 14 has a maximum chamber depth that is smaller than the spherical radius. Thus, the chamber bound is progressively flared outward as it extends up to the planar chamber opening 17. The spherical caps or bodies 15 protrude beyond only one side of a flange or reservoir plate 18, which is made in one part with caps 15. Caps 15 have intermediate spacings smaller than the width of their opening 17. Caps 15 each have an opening 17 at the side of plate 18 which is remote from body 15. The opening's side is also covered by the annular disk-shaped closure 16. The inner circumference of plate 18 has at least one driver 19, for example, a protuberance, a tooth or the like. Driver 19 engages unit 4 and is axially movable and withdrawable, and positively moves unit 4 in the rotation direction. Driver 19 carries reservoir 5 along when unit 4 is rotated about axis 10.

A piercing member 20 for destructing and opening closure 16 are provided in axis 11, within housing 2, 3 and between units 3, 4. Piercing member 20 opens closure 16 only in the vicinity of each single opening 17. Piercing member 20 is formed as one end of a discharge stud 21 freely protruding along axis 11 and having an outlet 7 at its free end face. The straight nozzle 21 has an outermost shell 22 conically tapered at an acute angle toward outlet 7. An inner shell 23 is radially spaced from and located within shell 22. Shell 23 is traversed over its full length up to outlet 7 by an outlet duct 24 which is at least 2 mm and at most 5 mm wide and has constant cross-sections throughout. The shells 22, 23 are of different lengths but they merge into each other at the outermost end of stud 21. Shell 23 protrudes in direction 13 beyond shell 22 and into unit 3. The inner end of shell 23 has in one part an opening member 25 such as a piercing or tearing member. Upon an axial or rotational motion about axis 10 member 16 may be burst open at that point where chamber 14 is aligned with axis 11. The central radial spacing of each chamber 14 from axis 10 of reservoir 5 equals the spacing between axes 10, 11. According to U.S. Pat. No. 5,469,989, issued Nov. 28, 1995, reservoir 5 may also work with plungers for the medium. Reference is made to this document for including the features and effects thereof in the present invention.

Unit 6 is mounted on unit 3 by a hinge 27 to be pivotable about an angle of precisely 90° or more. The hinge axis is oriented at right angles transverse to the common axial plane of axes 10, 11 and located between the outer and inner circumferences of unit 3. The shell 22 connects in one part and by its flared end to a planar end wall 26 which forms the end wall of unit 3 remote from unit 2. Wall 26 forms at its outside handle 28 provided with projections for higher gripping capacity. Handle 28 is squeezed to actuate unit 3. On the side of axis 10 which is remote from axis 11, wall 26 forms the associated bearing body for bearing 27. The axis of mount 27 may be close to the plane of handle 28. At the inside, wall 26 has a radially resilient snap member 29 protruding annularly along its outer circumference. Member 29 positionally secures unit 6 on unit 3 without motion play when unit 6 is in its operating position.

A rotational mechanism 30 is provided within unit 3 and between end wall 6 and unit 4. On each actuating stroke, the rotational mechanism 30 moves reservoir 5 with or without unit 4 about axis 10. Thus, the next chamber 14 still to be opened is aligned with axis 11. A sleeve or positioning member 31 protrudes from the inside of wall 26 in one part and in direction 13. Member 31 is directly juxtaposed with shell 22 and has rotating members distributed uniformly about its inner circumference, namely axial webs with laterally bevelled ends. Complementary positioning members 32 of the outer circumference of a sleeve project in opposite direction from unit 4 and may be either in one part with unit 4 or formed by a separate socket. A mutual actuating stroke of units 3, 4 causes one of the cited indexing steps of reservoir 5 because only then do members 31, 32 interengage. Members 31, 32 are closely surrounded by a permanently preloaded compression spring 33 annuarly supported with one end on an abutment 34 of the inside of wall 26. The other spring end annularly supports on reservoir 5 or part 16, 18. Thus reservoir 5 is pressed against unit 4. At the end of the stop-limited stroke of means 30 the member 32 is slightly spaced from wall 26.

Unit 3 forms a part 35 of the housing including an annular end wall 36 which connects to wall 26. An outermost shell 37 and an inner shell 38 freely project in direction 13 from wall 36. Shell 38 is located within and radially spaced from shell 37. Shell 38 is shorter than shell 37. Thus, from the inside of wall 36 a narrow annular groove emanates and is bounded by shells 37, 38 for being engaged by unit 2. This groove extends only over part of the length of shell 37 and over the full length of shell 38. Bearing 27 is located on the outside of wall 36. Wall 36 has a recess for receiving plate 26, which is entirely countersunk. Plate 26 also surrounds shell 22. Thus, the outsides of walls 26, 27 interconnect in a flush, coplanar and gapless manner. A counter member 39 protrudes along the inner circumference of this recess over wall 36. The interengaged snap seat of members 26, 36 and 29, 39 is pressure-tight and also provides a labyrinthine seal.

A downholder 40 axially positionally secures reservoir 5 on unit 4. The associated end of spring 33 is directly supported and centered on body 40. Instead of the design shown by full lines in the drawings, locking body 40 may additionally have the configuration 41 shown by dash-dotted lines. Body 40, 41 then has sleeve part 40 centered around axis 10 and sleeve part 41 centered around axis 11. For the air flowing through closure 9 between unit 4 and wall 26 the interengaging members 26, 31, 32, 40 form a dual duct or transverse deflection 42, namely first a deflection transverse to axis 10 and then between the circumferences of members 31, 32 a deflection back in direction 13. The flow velocity is greatly increased by correspondingly reduced flow cross-sections within this back deflection. Downstream of the back deflection all of the air is aimed against the bottom of a portion of the chamber 14 positioned near axis 11, namely radially outwards from the chamber portion closer to axis 10.

Thereby, in chamber 14 the flow causes a swirling or rotational flow about axis 10 or shell 23. The flow leaves chamber 14 as a helical flow directly into duct 24. For that, support 40 has an annular pressure and sealing end face 44 extending about axis 10. During rotation face 44 is supported with pretension and is stationary or moves slidingly on closure 16. Face 44 is traversed by a groove or transverse duct 43 oriented toward axis 11. The air flows through duct 43 after return deflection to be slantingly directed into the bottom of aligned chamber 14. The outer end of the holder 40 engages the outer circumference of body 31 by its inner circumference via a snap and sealing connector 45. On member 31 holder 40 is axially displaceable and either rotatable or prevented from rotation. At the stroke end of setting means 30 the support 40 may abut on the inside of wall 26 or on mount 34 causing a manifold increase of its support or pressing force. Support 40, 41 may also be in one part with spring 33, wall 26 or member 31, for example, as a bellows.

Embodiment 41 is expediently oval in axial view and connects spacedly between axes 10, 11 to the outer circumference of holder 40 in one part. At its end remote from reservoir 5 section 41 has an end wall permanently traversed by tube 23. This end wall has a lip sealingly sliding on the outer circumference of tube 23. Thus the sealing pressure increases with the fluid pressure within section 41. Also section 41 sealingly supports over its entire circumference with a pressure face 44 on closure 16 or plate 18. Face 44 of support 40 overengages opening 17 towards the opening's center axis. Section 41 also causes the air to pass narrow flow cross-sections while being oriented and aimed exclusively against the chamber 14 to be emptied. Thereby, the remaining chambers 14 or their closures 16 are not blown against.

Figure 4:
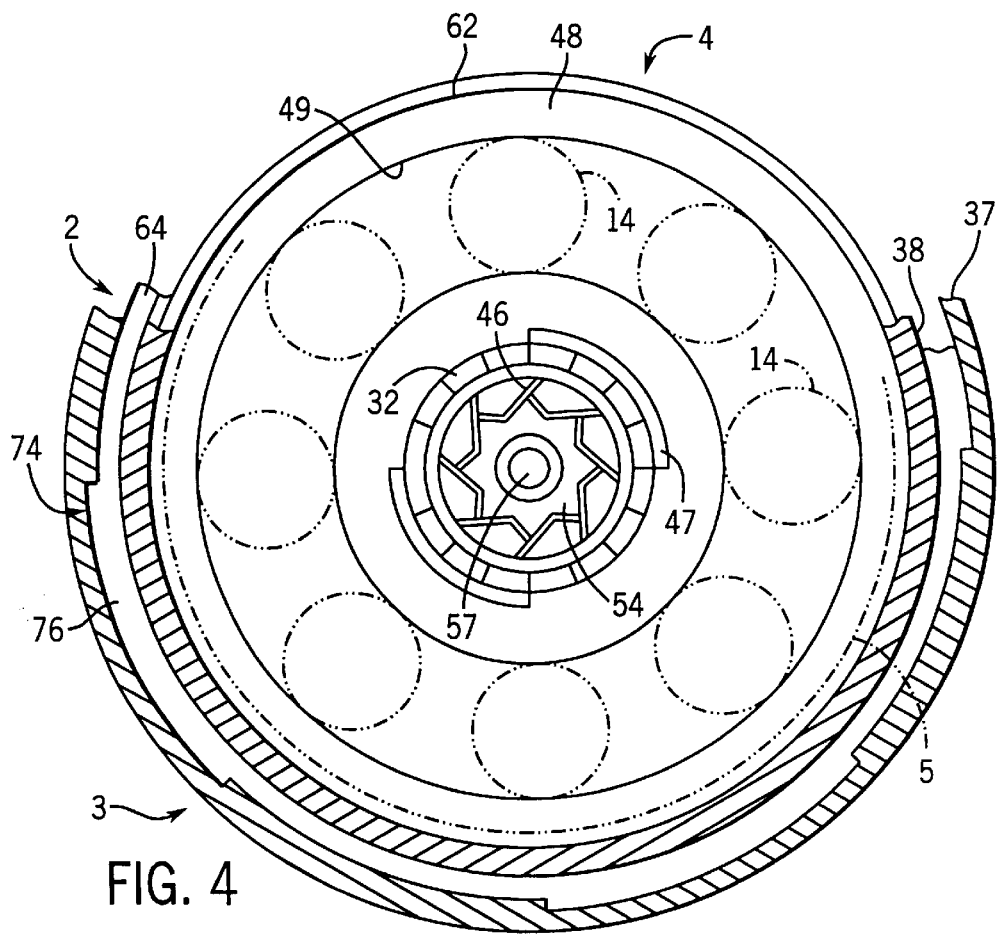
FIG. 4 is a transverse cross-sectional view looking downwards through the dispenser.

Sleeve member 32 is separate from and rotatable about axis 10 relative to the base body of unit 4. Member 32 connects to this base body via a rotor or freewheel coupling 46 which permits rotation of coupling member 32 relative to the base body codirectional with the indexing motion while positively preventing this rotation in the opposite direction. The radially inner coupling member of the base body may be a star having inclined, protruding, resiliently bendable locking arms shown in FIG. 4 and permitting rotation in one direction only. On its outer circumference coupling member 32 has a rotation driver 47 which is complementary to driver 19. Driver 47 has two radially protruding and circumferentially uniformly-distributed cams. Between the side flanks of these cams and about axis 10 the circumferentially equally sized cams of driver 19 engage without motion play radial to axis 10.

The one-part base body of unit 4 has an annular end wall 48 and a cylinder jacket 51 which protrudes from wall 48 in direction 13. Walls 48, 51 are located radially within shell 38 or axially displaceably but sealingly connect to the inner circumference of shell 38. Wall 48 has on its outside a recess 49 for receiving bodies 15. Recess 49 is formed by individual recesses which are circumferentially distributed for centering reservoir 5. Recess 49 may instead be a continuous annular groove about axis 10 for rotating reservoir 5. Each body 15 is continuously supported on recess 49 at least over a large spherical circle up to plate 18. Plate 18 fullfacedly supports on the outer end face of wall 48 and up to the driver elements 19 either about each individual recess or on both sides of groove recess 49. Also member 32 axially supports on this outer end face.

The inside of wall 48 forms an abutment 52 for a return or compression spring 59 which is significantly stronger and permanently higher pretensioned than spring 33. Spring 59 engages bearing 52 in being radially centered. A tubular casing 53 of closure 9 protrudes radially within bearing 52 beyond the inside of wall 48 and in direction 13. A hollow projection 54 protrudes beyond the outside of wall 48 and is a spigot of coupling 46. The star-shaped outer circumference of spigot 54 is provided with the coupling's resilient catch members which engage the inner circumference of member 32. Member 32 is either in one part with base body 4 or axially plugged and positionally locked without motion play on spigot 54 with a snap connector. This connector may simultaneously be a rotation bearing for rotating member 32 relative to body 4.

A movable closure and valve element 55 is located inside the free end of casing 53. Ball 55 is urged against its valve seat of housing 53 by a spring 56. The housing space of shells 53, 54 receives parts 55, 56 and forms a duct, which like shells 53, 54 is located in axis 10. This duct connects means 8 to duct 42. Shell 51 is surrounded by an outer shell 58 with a spacing from wall 48. Shells 51, 58 are radially spaced. Shell 88 also permanently supports on unit 2. Spring 59 is located within shells 51, 58.

The mutually opposed ends of shells 38, 58 provide drive or dragging means 60. The free end of shell 38 is a driver 61 and the shoulder 62 on the opposing end of shell 58 is the associated abutment. The inner circumference of shell 38 is sealingly guided at the outer circumference of body 4. In rest position faces of the driver and shoulder 61, 62 are mutually spaced by force of spring 33. This spacing corresponds to the operating stroke of piercing member 20 and rotational mechanism 30.

Like unit 3 also unit 2 forms a cup or housing from an end wall 63 and two nested shells 64, 65 which are radially interspaced and protrude from wall 63 only in direction 12.

The free end of inner shell 65 forms piston 66 or a piston lip which slides on the inner circumference of shell 51 up to wall 48. A valve casing 67 protrudes in axis 10 from bottom 64 only in direction 12 commonly with the associated parts of an inlet valve. Thus the means 8 form a compressing air pump 50, namely a thrust piston pump. On the return stroke pump 50 resucks air from without through ball or pressure relief valve 67. The outside of wall 63 forms the other handle 69 which for actuation is gripped commonly with handle 28 only single-handedly.

A valve control 70 is included for opening valve 9 irrespective of the stroke path of mechanisms 20, 30, 60 after a predetermined pumping stroke. Valve 9 could also open upon a predetermined overpressure in the pump chamber. Valve control 70 comprise in the axis of the member 55 a mandrel 71 which freely protrudes from parts 63, 67 in direction 12. Towards the end of the pump stroke mandrel 71 dives into the inlet opening of housing 53, abuts against and then drags ball 55 over a small opening stroke. Opening member 71 in this case is snap-mounted with a cap onto the free end of casing 67 to close this end.

Units 2, 3 are positively prevented from mutual withdrawal by a lock and a snap connector 73. Units 2, 3 are positively prevented from mutual rotation about axis 10 by a rotation lock 74. Also units 2, 3 are prevented from mutual withdrawal by snap lock 75. Therefore, shell 64 has at its free end a thickened edge bead 76 which continuously extends about the inner circumference of shell 64. On its outer circumference, bead 76 forms interspacedly protruding snap and anti-rotation members of locks 73, 74. For these members the inner circumference of shell 37 has grooves or locking recesses 74. Thus, at the free end of shell 37 and between the side flanks of each groove, a radially inwards protruding snap member 77 of lock 73 is formed. For lock 75 shell 58 has at its free end a snap member 78 which protrudes beyond its outer circumference. Member 78 slides circumferentially continuously and sealingly on the inner circumference of shell 64. Member 76 thus forms countermembers for three locks 73 to 75.

Between the circumferences of shells 51, 58 a narrow annular groove is formed. Both shells may be permanently supported with radial pretension on their counterfaces 66, 64. Same applies also to the relation of shells 37, 64. On the pump stroke shells 51, 58 dive into annular chamber 68 between shells 64, 65. At its bottom chamber 68 is bounded by transverse ribs which form a stop for the end of the pump stroke.

Parts 63 to 67 and 69 of unit 2 are made in one integrally formed part. Same applies to parts 36 to 39, 77 of unit 3 and to parts 48, 49, 51 to 54, 57, 58, 78 of unit 4. On unit 3 and in addition to parts 22 to 26, 28, 29 also parts 33, 40 may be integral to the one part body.

On actuation, the opening stroke, the pump stroke and the idle stroke of mechanisms 29, 30, 60 are commonly implemented. Before the rotational motion of mechanism 30 is completed, a spiked end 25 has already axially punctured the closure 16. Thus the further rotation up to axis 11 causes a transverse motion between spike 25 and closure 16 to better open the sealed caps 15. At the end of this stroke, spike 25 has not fully reached the bottom of chamber 14 while its inlet opening is located totally within chamber 14. Then mechanism 60 drags unit 4 synchroniously with unit 3 relative to unit 2. Thus, air is pretensioned in the pump chamber with valve 9 closed. Following the largest section 82 of pumping stroke 81 spigot 71 drags ball 55 synchronously into the opening position. Thus, the compressed air escapes valvelessly through duct 56 up to outlet 7 as described. Thereby member 76 passes over faces 61, 62. At the end of the stroke member 76 is located within the annular groove which is bounded by parts 36 to 38. On release of handle 28, 69 the mechanisms 9, 20, 30, 40, 50, 60, 70 return into their starting positions simultaneously under the force of springs 33, 56, 59. Then unit 4 needs not to be limited in its axial movement relative to unit 3. On the return motion valve 67 opens so that air is drawn in. Reservoir 5 need not execute a rotational motion during the return motion.

After all medium portions of reservoir 5 are discharged unit 6, as shown in FIG. 1, may be tilted open. Thereby parts 21, 25, 29, 31, 36, 40 follow to make parts 5, 32, 48, 49 freely accessible from above. Thus according to FIG. 1 reservoir 5 may be removed upwards or inserted in direction 13. All components cited may be injection-molded from plastic materials. All properties and effects may be provided precisely as described, or merely substantially or approximately so and may also greatly deviate therefrom depending on the particular requirements. The spacing between handles 28, 69 may equal the largest outer diameter of dispenser 1. Expediently each of these dimensions amounts to maximally 70 or 60 mm, the dimensional relationships as shown being particularly favorable. Units 3 to 6 are particularly easy to assemble. Unit 3 overengages units 2, 4 and unit 2 overengages unit 5 in each case at the outer circumference to provide a lid.

What is claimed is:

1. A dispenser for applying media, comprising:
    a base (2, 3) including a first base unit (2) formed around a central axis, and having a second base unit (3) displaceable with respect to said first base unit (3) in an operating motion in at least an axial direction from a starting position to an end position, said first base unit (2) including a first base body (63 to 65) and said second base unit (3) including a second base body (36 to 38), said base (2,3) having an interior portion;
    means contained in said interior portion of said base (2, 3) for supporting a medium reservoir (5) including at least one reservoir chamber (14) hermetically sealed at a reservoir opening (17);
    a medium outlet (7) communicating with said base interior for discharging the medium, and
    at least one outlet closure (9,16) sealingly separating at least one of the media from said medium outlet (7), and
    wherein means (60) are provided for displacing said reservoir (5) relative to said base (2, 3) in at least one of an axial direction and a rotational direction commonly with said operating motion.

2. The dispenser according to claim 1, wherein the media include a first medium stored in a reservoir chamber (14) and a second medium, means being included for flow feeding the second medium within said base (2, 3).

3. The dispenser according to claim 1 and wherein said means for supporting includes a reservoir support (4), wherein said reservoir (5) is removably disposed on said reservoir support (4).

4. The dispenser according to claim 3, wherein said reservoir support (4) is mounted to be movable relative to both said first and second base units (2, 3) in an axial direction and a rotational direction which are mutually transversely oriented.

5. The dispenser according to claim 1, wherein said reservoir (5) includes a medium capsule assembled from a capsule cup (15) and cup lid (16) sealingly closing said reservoir opening (17) and openable by destruction.

6. The dispenser according to claim 1, wherein said reservoir (5) is displaceable substantially parallel to said operating motion (13).

7. The dispenser according to claim 1, wherein said operating motion defines a stroke path including a path section, said medium reservoir (5) being movable only over said path section (81) with respect to both said first and second base units (2, 3).

8. The dispenser according to claim 7, wherein said stroke path further includes an additional path section (80), said medium reservoir (5) being displaceable over said additional path section (80) with respect to exclusively one of said first and second base units (2, 3).

9. The dispenser according to claim 8, wherein said path section (80) is closer to said starting position than said additional path section (81).

10. The dispenser according to claim 2, wherein means (20) are included for single-sidedly opening said reservoir chamber (14) over only a first path section (80) of said operating motion and for pretensioning the second medium over a second path section (81) of said operating motion.

11. The dispenser according to claim 2, wherein said reservoir chamber (14) is eccentric to said outlet closure (9) blocking the second medium.

12. The dispenser according to claim 2, wherein at least one transverse deflection (42, 43) including a return deflection is provided for the second medium and ports directly into said medium reservoir (5) upstream of said reservoir chamber (14) when opened.

13. The dispenser according to claim 1, wherein said medium reservoir (5) includes a reservoir plate (18) externally circumferentially protruding beyond said reservoir chamber (14) and substantially constantly thick, said reservoir chamber (14) forming a portion of said medium reservoir (5) which protrudes transversely beyond said reservoir plate (18).

14. The dispenser according to claim 1, wherein said reservoir opening (14) is bounded by flanks which are inclined in axial cross-section.

15. The dispenser according to claim 2, wherein a pressure chamber is included for receiving the second medium, said pressure chamber including a pump chamber of a pump (50), said pressure chamber being bounded by two mutually displaceable bounds including a cylinder (51) and an impeller (66).

16. The dispenser according to claim 15, wherein said medium reservoir (5) is displaceable commonly with said cylinder (51) and said medium outlet (7) relative to said first base unit (2) with said operating motion.

17. The dispenser according to claim 3, wherein said second base unit (3) includes a driver (61) and said reservoir support (4) includes a counter stop (62) positively driven by said driver (61), when in said starting position said driver (61) being spaced from said counter stop (62).

18. The dispenser according to claim 2, wherein control means (70) are included for mechanically positively opening said outlet closure (9) which blocks the second medium, said control means (70) being driven by said operating motion.

19. The dispenser according to claim 18, wherein said first base unit (2) includes a mandrel (71) opening said outlet closure (9) shortly before attaining said end position.

20. The dispenser according to claim 18, wherein said outlet closure (9) is a pressure-relief valve including a reciprocating valve body (55).

21. The dispenser according to claim 1, wherein return means (33, 59) are included and return said first and second base units (3 to 4) from said end position to said starting position.

22. The dispenser according to claim 21, wherein said return means include at least one spring (33, 59) acting directly on said medium reservoir (5).

23. The dispenser according to claim 21, wherein said return means include a first spring (59) acting on said first base unit (2) and said medium reservoir (5), said return means including a second spring (33) acting on said medium reservoir (5) and said second base unit (3), said first spring (59) being stronger than said second spring (33).

24. The dispenser according to claim 8 and further including setting means (30) positioning said reservoir chamber (14) from an initial position to a standby position, in which the medium reservoir (5) is aligned with said medium outlet for being directly emptied by a flow through said reservoir chamber (14), wherein said setting means (30) include a positioning drive (31, 32) translating said operating motion into a transverse motion of said medium reservoir (5), said reservoir chamber (14) including a plurality of separate chambers (14) sequentially transferable into said standby position by said setting means (30) while said dispenser (1) is manually operated over said path section (81).

25. The dispenser according to claim 3 and further including a positioning member (40, 41) resiliently locking said medium reservoir (5) against said reservoir support (4), wherein an outlet (57) for a second medium is located upstream of said reservoir chamber (14) and ports into said positioning member (40, 41).

26. The dispenser according to claim 25, wherein said positioning member (40, 41) covers said reservoir chamber (14) while being emptied and guides the second medium directly into said reservoir chamber (14), said positioning member (40, 41) being displaceably mounted on said second base unit (3) including said medium outlet (7).

27. The dispenser according to claim 1 and further including a casing with a casing lid (6) operationally entirely enveloping said medium reservoir (5) and assembled from said first and second base units (2, 3), wherein said casing lid (6) is openable to provide a charge opening for exchanging said medium reservoir (5) without disassembling said first and second base units (2, 3), said first and second base units (2, 3) including guide members (76 to 78) displaceably interengaged and spaced from said charge opening.

28. The dispenser according to claim 27, wherein said casing includes an end wall (26) including said casing lid (6), said casing lid (6) being openable away from said medium reservoir (5).

29. The dispenser according to claim 27, wherein said casing lid (6) includes at least one of
   said medium outlet (7), and
   a guide body (40, 41) guiding an auxiliary medium flow into said reservoir chamber (14) and towards said medium outlet (7).

* * * * *